United States Patent [19]

Goldstein et al.

[11] 4,118,586

[45] Oct. 3, 1978

[54] PROCESS FOR PREPARING DIHYDROXYTOLUENE

[75] Inventors: Stephen L. Goldstein, Cheshire; John S. Babiec, Jr., Orange, both of Conn.

[73] Assignee: Olin Corporation, New Haven, Conn.

[21] Appl. No.: 832,306

[22] Filed: Sep. 12, 1977

[51] Int. Cl.² ............................................. C07C 37/10
[52] U.S. Cl. .................................................... 568/767
[58] Field of Search ........ 260/621 M, 621 R, 453 PH

[56] References Cited

U.S. PATENT DOCUMENTS

| | | | |
|---|---|---|---|
| 3,128,310 | 4/1964 | Koch | 260/582 |
| 3,331,876 | 7/1967 | Van Horn | 260/453 PH |
| 3,350,438 | 10/1967 | Henning | 260/453 PH |
| 3,462,497 | 8/1969 | Greco | 260/621 M |
| 3,799,963 | 3/1974 | Adams | 260/453 SP |
| 3,933,925 | 1/1976 | Greco | 260/621 M |

*Primary Examiner*—James O. Thomas, Jr.
*Assistant Examiner*—Werren B. Lone
*Attorney, Agent, or Firm*—F. A. Iskander; Robert J. Feltovic; Thomas P. O'Day

[57] ABSTRACT

A process for preparing dihydroxytoluene by heating toluene diisocyanate distillation residue in the presence of an aqueous solution of phosphoric acid.

10 Claims, No Drawings

PROCESS FOR PREPARING DIHYDROXYTOLUENE

BACKGROUND OF THE INVENTION

1. Field of the Invention

This invention relates to a process wherein the residue, which is obtained from the distillation of the product of phosgenating toluene diamine to toluene diisocyanate, is used to produce dihydroxytoluene.

Dihydroxytoluene is a known chemical which is used in certain medicinal applications and as a reagent for carbohydrates. It is also of potential utility in the production of plastic resins.

Toluene diisocyanate is produced on a large commercial scale by a process which comprises reacting toluene diamine with excess phosgene usually in the presence of an organic solvent medium. An illustrative process is disclosed in U.S. Pat. No. 3,287,387. Along with toluene diisocyanate, the phosgenation product mixture usually comprises unreacted phosgene, solvent, hydrogen chloride by-product, and a relatively substantial proportion of side reaction products in the form of residual and high-boiling materials.

Recovery of a substantial or major proportion of toluene diisocyanate from this mixture is achieved by distillation which is usually effected in two or more steps to enable removal of the low-boiling components, e.g., the phosgene and solvent first before recovering the toluene diisocyanate. The remaining residue from distillation is a solid or viscous mixture which is often discarded.

2. Description of the Prior Art

In order to recover toluene diamine values from the residue of the distillation of the product of phosgenating toluene diamine, U.S. Pat. Nos. 3,128,310 and 3,331,876 disclose the concept of reacting the residue with water in the presence of alkali.

U.S. Pat. No. 3,462,497 discloses the use of phosphoric acid in the hydrolysis of phenylene diamine to resorcinol; and U.S. Pat. No. 3,933,925 discloses the hydrolysis of toluene diamine to methyl resorcinol in the presence of ammonium bisulfate.

Further in the prior art, U.S. Pat. No. 3,799,963 discloses a process for reducing the acidity and hydrolyzable chloride content of toluene diisocyanate by heating it in the presence of formic acid, and U.S. Pat. No. 3,350,438 discloses the preparation of biuret polyisocyanates by the reaction of organic polyisocyanates with formic acid.

SUMMARY OF THE INVENTION

Now a simple process has been found whereby dihydroxytoluene can be prepared directly from the residue of the distillation of the product of phosgenating toluene diamine. According to the invention this is achieved by heating the residue in the presence of an aqueous solution of phosphoric acid under select conditions as described in more detail hereinbelow.

DETAILED DESCRIPTION

The process of the invention can be employed using any residue which results from the distillation of the product of phosgenating toluene diamine. As commonly used in the commercial production of toluene diisocyanate, the toluene diamine is typically made up of a mixture 2,4- and 2,6-isomers and may in addition contain traces of ortho-toluene diamine. The distillation residue is usually a solid or dark, viscous liquid which is substantially free of solvent. Along with varying amounts of phosgene, by-product hydrochloric acid, and a residual content, up to about 60% by weight, of toluene diisocyanate, it usually contains a substantial amount, e.g., 25-70% by weight, of high boiling and tarry by-products of the phosgenation reaction.

Preferably, when in viscous liquid form or in large solid chunks, the residue should initially be subjected to preparatory treatment in order to transform it to subdivided form. This can be achieved using conventional techniques. For example, the viscous liquid may be dried and solidified, and the solid chunky residue may be subjected to the action of a grinder or high-shear mixer whereby it is transformed into small granules or powder.

The other reactant which is employed in practicing the process of the invention is an aqueous solution of phosphoric acid. Ordinarily, the phosphroic acid concentration of such a solution should be no higher than about 50 percent by weight. For example, the concentration may range from about 5 to about 50 percent and more preferably about 15-35 percent, by weight.

Preferably the aqueous phosphoric acid solution is prepared before being combined and mixed with the residue. However, if desired, the solution may be prepared in situ by first combining the water with the residue followed by gradual addition of the requisite amount of phosphoric acid.

The relative proportion of aqueous phosphoric acid solution which is used per unit weight of residue may be varied within a reasonably wide range depending on the exact composition of the residue and on the phosphoric acid concentration in the solution. Generally speaking, such a proportion of the aqueous solution may be employed as to provide the equivalent of from about 0.001 to about 0.3 gram-moles of pure phosphoric acid (100 percent $H_3PO_4$) per every gram of residue. As a practical matter, however, it is preferred to employ such relative amounts as to provide about 0.005–0.10, and more preferably about 0.10–0.05, gram-moles of phosphoric acid per gram of residue.

In accordance with the invention, dihydroxytoluene is formed by heating the residue-aqueous phosphoric acid mixture. It is contemplated that any suitable elevated temperature may be employed which is effective in achieving this objective without any adverse effect on the reaction mixture or the product thereof. Illustratively, the mixture may be heated to a temperature ranging from about 180° C. to about 270° C. As a practical matter, a temperature range of about 200–260 is preferred; and in accordance with the most preferred embodiments of the invention, a temperature of about 210–240 is employed.

The pressure used in carrying out the reaction is not critical. Thus the formation of dihydroxytoluene in accordance with the process of the invention can be achieved under any suitable pressue so long as a temperature within the above-specified range is attained. In actual practice, it is preferred to carry out the process of the invention in a sealed reactor or vessel, e.g., an autoclave or high pressure bomb, and this necessitates operation under super-atmospheric pressure. Pursuant to this preferred embodiment, the pressure under which the reaction is carried out may range from about 200 to about 1500 psig, and more preferably about 500 to about 1000 psig.

Completion of the reaction of the residue with the aqueous phosphoric acid solution, which usually takes about 5–10 hours, is achieved when no more dihydroxytoluene is formed. At this point, further heating will no longer be necessary and in fact should be avoided in order to prevent or minimize undesirable polymerization. Thus the mixture, which will be comprised of an aqueous solution containing dihydroxytoluene, ammonium phosphate, ortho-toluene diamine and possibly varying amounts of unreacted acid, residual material and other by-products, is allowed to cool down. Recovery of the dihydroxytoluene product is finally achieved by any suitable or conventional method such as by extraction with a suitable organic solvent, e.g, ethyl ether. Moreover, it has been found that the presence of the ortho-toluene diamine does not interfere with such recovery which can be achieved fairly easily and rapidly. So recovered, the dihydroxytoluene may be used as such as a chemical intermediate or it may optionally be further purified for use in those applications where a highly pure product is required.

The process of the invention provides a practical means for preparing dihydroxytoluene, a valuable chemical intermediate, from the toluene diisocyanate distillation residue which might otherwise be discarded. Moreover, this objective is achieved by a simple and direct route involving a single reactive step, the main product of which, moreover, can be easily recovered by simple solvent extraction.

By virtue of the above advantages, the process described herein constitutes a potentially valuable addition or modification in the commercial process for making toluene diisocyanate.

The following examples are provided to illustrate the invention. In these examples, all parts and percentages are by weight unless otherwise specified.

Further in the examples, the toluene diisocyanate distillation residue which is referred to and used was obtained by a conventional method, as described for example in U.S. Pat. No. 3,287,387 to Denton et al, for the commercial production of toluene diisocyanate. More specifically, this method involves (a) reacting, at about 125° C., excess phosgene with a solution of toluene diamine (mixture of 2,4- and 2,6-isomers) in monochlorobenzene solvent, (b) removing the monochlorobenzene, and most of the unreacted phosgene and by-product HCl from the phosgenation product, and (c) further distilling the remaining product to recover overhead pure toluene diisocyanate. The residue from this distillation, which contains about 30 percent by weight of residual toluene diisocyanate, is used in the examples.

EXAMPLE I

An aqueous solution of phosphoric acid was prepared by adding 223.6 grams of 85% $H_3PO_4$ to 353 grams of water. To this solution there were added 71.4 grams of finely divided toluene diisocyanate distillation residue. The mixture was heated to 230° C. for 6 hours in an autoclave in which a pressure of 900 psig was observed. Thereafter, the reaction mixture was allowed to cool down to room temperature and then the dihydroxytoluene product was extracted with three 300 ml. portions of ethyl ether. The extracts were combined and the ether was evaporated leaving a crude oily product. This was distilled at 115° C. and 0.15 m.m. of mercury pressure to give 26.8 grams of solid product which, on analysis by vapor phase chromatography, was found to consist mainly of 82% 2,4-dihydroxytoluene and 18% of 2,6-dihydroxytoluene.

EXAMPLE II

Powdered toluene diisocyanate distillation residue (50 grams) was added, in three portions over a 30-minute period, to a refluxing solution of 110 grams of 85% $H_3PO_4$ in 600 mls. of water. The resulting mixture was transferred to a high pressure bomb and heated to 220°–240° C. for six hours. The resulting solution, after cooling to room temperature, was filtered and the dihydroxytoluene product in the filtrate was extracted with three 150 mls. portions of ethyl ether. The extracts were combined and the ether solvent was evaporated leaving an oily residue. Distillation of the oil gave 24.3 grams of a solid product which, on analysis by vapor phase chromatography, was found to consist of 85% of 2,4-dihydroxytoluene and 15% of 2,6-dihydroxytoluene.

What is claimed is:

1. A process for preparing dihydroxytoluene from the distillation residue obtained from the distillation of the product of phosgenating toluene diamine to form the corresponding diisocyanate, which process comprises heating said distillation residue to a temperature of about 180°–270° C. in the presence of an aqueous solution of phosphoric acid in which the concentration of said acid ranges from about 5 to about 50% by weight, said aqueous solution being employed in such a proportion as to provide the equivalent of about 0.001 to about 0.3 gram-moles of phosphoric acid per gram of said residue.

2. The process of claim 1 wherein said temperature ranges from about 210° to about 240° C.

3. The process of claim 1 wherein said phosphoric acid concentration ranges from about 15 to about 35% by weight.

4. The process of claim 1 wherein the proportion of said solution is such as to provide the equivalent of about 0.01–0.05 gram-moles of phosphoric acid per every gram of said residue.

5. The process of claim 1 wherein said residue is in granular or powder form.

6. The process of claim 5 wherein super-atmospheric pressure is employed.

7. The process of claim 6 wherein the proportion of said solution is such as to provide the equivalent of about 0.005–0.10 gram-moles of phosphoric acid per gram of residue.

8. The process of claim 7 wherein said temperature is about 200°–260° C. and said phosphoric acid concentration is about 15–35% by weight.

9. The process of claim 8 wherein said temperature is about 210°–240° C. and said pressure is about 500–1000 psig.

10. The process of claim 9 wherein the proportion of said aqueous solution is such as to provide the equivalent of about 0.01–0.05 gram-moles of phosphoric acid per gram of said residue.

* * * * *